United States Patent [19]

Kurita et al.

[11] Patent Number: 5,863,909
[45] Date of Patent: Jan. 26, 1999

[54] ADJUVANT COMPOSITION FOR AGRICULTURAL CHEMICALS AND METHOD FOR ENHANCING THE EFFICACY OF AGRICULTURAL CHEMICAL

[75] Inventors: Kazuhiko Kurita; Keiko Hasebe; Katsuhiko Yamaguchi; Masaharu Hayashi; Yuichi Hioki, all of Wakayama, Japan

[73] Assignee: Kao Corporation, Tokyo, Japan

[21] Appl. No.: 836,719

[22] PCT Filed: Nov. 22, 1995

[86] PCT No.: PCT/JP95/02382

§ 371 Date: May 22, 1997

§ 102(e) Date: May 22, 1997

[87] PCT Pub. No.: WO96/16539

PCT Pub. Date: Jun. 6, 1996

[30] Foreign Application Priority Data

Nov. 25, 1994 [JP] Japan ................................ 6-291767

[51] Int. Cl.⁶ .................... A01N 25/30; A01N 43/78; A01N 57/14; B01J 13/00
[52] U.S. Cl. .................. 514/129; 71/DIG. 1; 252/312; 252/355; 252/356; 514/369; 514/399; 514/941; 514/952; 514/975

[58] Field of Search .................. 252/312, 355, 252/356; 71/DIG. 1; 424/405; 514/941, 952, 975, 129; 504/116

[56] References Cited

U.S. PATENT DOCUMENTS

| | | | |
|---|---|---|---|
| 2,731,338 | 1/1956 | Fike et al. | 252/355 X |
| 2,786,013 | 3/1957 | Behrens | 252/312 X |
| 3,074,791 | 1/1963 | Scoles | 71/DIG. 1 |
| 5,178,795 | 1/1993 | Roberts | 252/356 |
| 5,236,624 | 8/1993 | Lepert et al. | 252/312 X |

FOREIGN PATENT DOCUMENTS

| | | |
|---|---|---|
| 0498785A1 | 8/1992 | European Pat. Off. . |
| 62-43968 | 9/1987 | Japan . |
| 6145003 | 5/1994 | Japan . |

*Primary Examiner*—Richard D. Lovering
*Attorney, Agent, or Firm*—Birch, Stewart, Kolasch & Birch, LLP

[57] ABSTRACT

An adjuvant composition for agricultural chemicals comprising at least one sorbitan/fatty acid ester surfactant (A) and at least one surfactant (B) selected from the group consisting of resin acid surfactants and anionic oligomer or polymer type quaternary ammonium salt surfactants can be used for various crops in safety without causing injury thereof to the crops, and can enhance the efficacies of various agricultural chemicals.

26 Claims, No Drawings

ADJUVANT COMPOSITION FOR AGRICULTURAL CHEMICALS AND METHOD FOR ENHANCING THE EFFICACY OF AGRICULTURAL CHEMICAL

This application is a National Phase Filing under 35 U.S.C. § 371 of International Application No. PCT/JP95/02382, filed Nov. 22, 1995 which claims priority based on Japanese Application No. 6-291767, filed Nov. 25, 1994.

BACKGROUND OF THE INVENTION

1. Field of the Invention

The present invention relates to a novel adjuvant composition for agricultural chemicals, a method for enhancing the efficacies of agricultural chemicals which comprises using said composition together with an agricultural chemical, a use of said composition for enhancing the efficacies of agricultural chemicals and a novel agricultural chemical composition.

2. Description of the Related Art

Agricultural chemicals including insecticides, fungicides (or bactericides), herbicides, miticides (or acaricides) and plant growth regulators have been used in the forms of, for example, emulsions, wettable powders, granules, dusts and flowables. In the properties of these agricultural chemical preparations, various attempts have been made to achieve the maximum efficacy of the agricultural chemical. However, it has been difficult to enhance the efficacies of agricultural chemicals through adjustments in formulations. It is further difficult to develop novel agricultural chemicals. Therefore, further enhancement of the efficacies of existing agricultural chemicals would highly contribute to the industry.

As substances capable of enhancing the efficacies of agricultural chemicals, surfactants comprising various nitrogen-containing compounds such as quaternary ammonium salts, betaines and amine oxides have been known. It is known that quaternized or further polyoxyethylenated long-chain amines, among the above-mentioned compounds, are effective for this purpose. However, the effects of the above-described surfactants comprising the nitrogen-containing compound capable of enhancing the efficacies of agricultural chemicals are not always satisfactory.

On the other hand, Japanese Patent Publication-B No. 62-43968 (published on Sep. 17, 1987) and Japanese Patent Publication-A No. 6-145003 (published on May 24, 1994) disclose the use of a sorbitan/fatty acid ester as an ingredient of an agrohorticultural pest control composition and the use of a polyoxyalkylene/resin acid ester as an ingredient of an adjuvant for an agrohorticultural biocide, respectively. However, one of the sorbitan/fatty acid ester and the polyoxyalkylene/resin acid ester exhibits an insufficient effect for enhancing the efficacies of agricultural chemicals.

DISCLOSURE OF THE INVENTION

SUMMARY OF THE INVENTION

The present inventors have made extensive studies for the purpose of finding a compound capable of enhancing the efficacies of agricultural chemicals. As the result of the studies, the present inventors have found that a mixture comprising a sorbitan/fatty acid ester surfactant and a resin acid surfactant or an oligomer or polymer type quaternary ammonium salt surfactant can enhance the efficacies of various agricultural chemicals. The present invention has been accomplished on the basis of this finding.

Thus, the present invention relates to an adjuvant composition for agricultural chemicals comprising at least one sorbitan/fatty acid ester surfactant (A) and at least one surfactant (B) selected from the group consisting of resin acid surfactants and quaternary ammonium salt surfactants represented by the following formula:

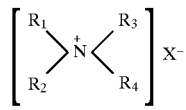

wherein at least one of $R_1$, $R_2$ and $R_3$ represents a linear or branched alkyl or alkenyl group having 8 to 30 carbon atoms, and the rest of them represent(s) one or two groups selected from the group consisting of —$CH_3$, —$CH_2CH_3$,

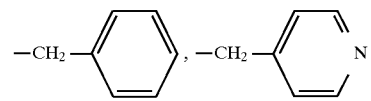

and

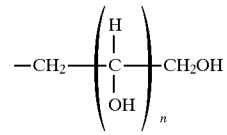

(n being a number of 1 to 5), $R_4$ represents —$CH_3$ or —$CH_2CH_3$, and the counter ion, $X^-$, represents an anionic group derived from an anionic oligomer or polymer having a weight average molecular weight of 300 to 20,000 and selected from the group consisting of (1) (co)polymers obtained by polymerizing a monomer(s) which comprises at least one member selected from the group consisting of unsaturated carboxylic acids and derivatives thereof as the indispensable component, (2) (co)polymers obtained by polymerizing a monomer(s) which comprises styrene-sulfonic acid as the indispensable component, and (3) condensates of a sulfonated aromatic compound which may have a hydrocarbon group(s) as a substituent with formaldehyde.

Further, the present invention relates to a method for enhancing the efficacy of an agricultural chemical, which comprises applying a sorbitan/fatty acid ester surfactant (A) and at least one surfactant (B) selected from the group consisting of resin acid surfactants and quaternary ammonium salt surfactants described above together with an agricultural chemical to a locus which would benefit from such treatment.

Furthermore, the present invention relates to a use of a mixture of a sorbitan/fatty acid ester surfactant (A) with at least one surfactant (B) selected from the group consisting of resin acid surfactants and quaternary ammonium salt surfactants described above for enhancing the efficacy of an agricultural chemical.

In addition, the present invention relates to an agricultural chemical composition comprising at least one sorbitan/fatty acid ester surfactant (A), at least one surfactant (B) selected from the group consisting of resin acid surfactants and quaternary ammonium salt surfactants described above, and an agricultural chemical, wherein the weight ratio of the sum of surfactant (A) and surfactant (B) to the agricultural chemical is 0.03 to 50.

Further scope and applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTOPN OF THE INVENTION

[Adjuvant composition for agricultural chemicals]

Examples of the sorbitan/fatty acid ester surfactants (A) to be used in the present invention include sorbitan/fatty acid esters and polyoxyalkylene sorbitan/fatty acid esters, i.e., alkylene oxide adducts of sorbitan fatty acid esters. The sorbitan/fatty acid esters are particularly preferably used in the present invention.

Although the sorbitan/fatty acid ester may be any one of a monoester, a diester and a triester, usually a mixture of these esters is used. The use of a sorbitan/fatty acid ester mixture having a monoester content of 40 to 70% by weight is desirable in the present invention. The fatty acid moiety of the sorbitan/fatty acid ester is preferably a fatty acid residue derived from a fatty acid having 8 to 22 carbon atoms. Specific examples of the fatty acids having 8 to 22 carbon atoms include capric acid, lauric acid, palmitic acid, oleic acid and stearic acid.

The polyoxyalkylene sorbitan/fatty acid esters are produced by, for example, a process wherein an alkylene oxide(s) is(are) added to sorbitan to thereby introduce an oxyalkylene (or alkyl ether) group(s) and then the resultant compound is esterified by reacting it with a fatty acid. Examples of the alkylene oxides used for the addition reaction include ethylene oxide, propylene oxide and butylene oxide, among which ethylene oxide is particularly preferred. The average number of moles of the alkylene oxide added is usually 2 to 30 mol, preferably 5 to 25 mol, per mole of the sorbitan/fatty acid ester.

The resin acid surfactant and/or quaternary ammonium salt surfactant (B) is used together with the above-described sorbitan/fatty acid ester surfactant (A) in the present invention.

The resin acid surfactant to be used in the present invention refers to a surfactant produced from a resin acid or rosin.

The rosin herein refers to a natural resin mainly comprising resin acids which are contained in a residue obtained by distilling a resin oil from a pinaceous plant to thereby remove volatile substances such as an essential oil. Examples of the main resin acids constituting such a natural resin include abietic acid and analogues thereof, and pimaric acid. Commercially available rosins are usable as the starting material for the resin acid surfactant in the present invention, though the constituents and properties of rosins vary to some extent, since they are derived from natural products. Among the rosins, those available under the name of "tall rosin" are particularly preferred. Examples of the commercially available tall rosins include Hartall Rosin R-X, Hartall Rosin R-WW and Hartall Rosin R-N (products of Harima Chemicals, Inc.).

The resin acid surfactant to be used in the present invention is preferably a polyoxyalkylene rosin ether, i.e., an alkylene oxide adduct of rosin, or a polyoxyalkylene resin acid ether, i.e., an alkylene oxide adduct of a resin acid. The polyoxyalkylene rosin ether is synthesized by adding an alkylene oxide to a rosin. The polyoxyalkylene resin acid ether is synthesized by adding an alkylene oxide to a resin acid. In the present invention, those obtained by adding, on average, preferably 2 to 50 mol, still more preferably 5 to 40 mol and most preferably 8 to 30 mol, per mol of a rosin or a resin acid, of an alkylene oxide to the rosin or resin acid are used. In the addition reaction, ethylene oxide or a combination of ethylene oxide with another alkylene oxide is preferably used as the alkylene oxide.

Examples of the commercially available resin acid surfactants include Hartall REO-15 and REO-30 (rosin ethoxylates of Harima Chemicals, Inc.); and BLAUNON REO-8 [polyoxyethylene (8) rosin ether], REO-15 [polyoxyethylene (15) rosin ether] and REO-30 [polyoxyethylene (30) rosin ether] (products of Aoki Yushi Kogyo K.K.).

The quaternary ammonium salt surfactants to be used in the present invention are those represented by the following formula:

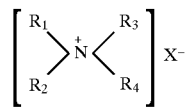

wherein at least one of $R_1$, $R_2$ and $R_3$ represents a linear or branched alkyl or alkenyl group having 8 to 30 carbon atoms, and the rest of them represent(s) one or two groups selected from the group consisting of —$CH_3$, —$CH_2CH_3$,

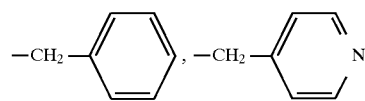

and

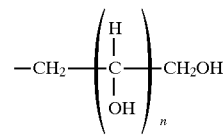

(n being a number of 1 to 5), $R_4$ represents —$CH_3$ or —$CH_2CH_3$, and the counter ion, $X^-$, represents an anionic group derived from an anionic oligomer or polymer having a weight average molecular weight of 300 to 20,000 and selected from the group consisting of (1) (co)polymers obtained by polymerizing a monomer(s) which comprises at least one member selected from the group consisting of unsaturated carboxylic acids and derivatives thereof as the indispensable component, (2) (co)polymers obtained by polymerizing a monomer(s) which comprises styrenesulfonic acid as the indispensable component, and (3) condensates of a sulfonated aromatic compound which may have a hydrocarbon group(s) as a substituent with formaldehyde.

The quaternary ammonium salt surfactants vary depending on the types of the functional groups $R_1$ to $R_4$ and the counter ion, $X^-$ in the above formula. Any of these quaternary ammonium salt surfactants is usable in the present invention. A mixture of two or more of the quaternary ammonium salt surfactants described above is also usable.

A specific description will now be made as to the anionic oligomers or polymers (1) to (3) providing the counter ion of the quaternary ammonium salt surfactant.

(1) (Co)polymers obtained by polymerizing a monomer(s) which comprises at least one member selected from the group consisting of unsaturated carboxylic acids and derivatives thereof as the indispensable component:

Examples of the monomers (i.e., at least one member selected from the group consisting of unsaturated carboxylic acids and derivatives thereof) indispensable for the production of the (co)polymer (1) include unsaturated monocarboxylic acids such as acrylic acid and methacrylic acid, unsaturated dicarboxylic acids such as maleic acid, and their derivatives, such as alkyl esters (e.g., methyl esters) and ethylene oxide adducts of the above-described carboxylic acids and ethylene oxide adducts of the alkyl esters of the above-described carboxylic acids. Examples of the monomers (comonomers) which may be used with the above-described indispensable monomers include vinyl acetate, isobutylene, diisobutylene and styrene.

These monomers are polymerized by any process known hitherto. The relative amounts (proportions) of the monomers and the degree of polymerization of the (co)polymer are not particularly limited.

Examples of the (co)polymers (1) include an acrylic acid polymer, a methacrylic acid polymer, an acrylic acid/methacrylic acid copolymer, an acrylic acid/methacrylic acid polyoxyethylene ether copolymer, an acrylic acid/methyl acrylate copolymer, an acrylic acid/vinyl acetate copolymer, an acrylic acid/maleic acid copolymer, a maleic acid/isobutylene copolymer and a maleic acid/styrene copolymer.

A mixture of two or more of these (co)polymers may be used as the anionic oligomer or polymer which provides the counter ion of the above-described quaternary ammonium salt surfactant in the present invention. A part of the carboxyl groups of these oligomers or polymers may form an alkali metal salt, ammonium salt or organic amine salt thereof, as long as the desired properties are not impaired.

The (co)polymer (1) to be used in the present invention has a weight average molecular weight of 300 to 20,000.
(2) (Co)polymers obtained by polymerizing a monomer(s) which comprises styrenesulfonic acid as the indispensable component:

The styrenesulfonic acid homopolymer can be easily produced by polymerizing styrenesulfonic acid or by sulfonating a polystyrene. The styrenesulfonic acid polymer comprises a constitutive unit of the following formula:

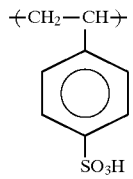

A styrenesulfonic acid homopolymer to be used as the anionic oligomer or polymer providing the counter ion of the above-described quaternary ammonium salt surfactant in the present invention is one having a weight average molecular weight of preferably 300 to 20,000, still more preferably 300 to 10,000.

The copolymer comprising the styrenesulfonic acid units and other monomer units can be easily produced by copolymerizing styrenesulfonic acid with another monomer or by sulfonating a copolymer composed of styrene units and other monomer units. Examples of the comonomers providing other monomer units include hydrophobic monomers such as alkyl acrylates, alkyl methacrylates, vinyl alkyl ethers, vinyl acetate, ethylene, propylene, butylene, butadiene, diisobutylene, vinyl chloride, vinylidene chloride, acrylonitrile and styrene, and hydrophilic monomers such as acrylic acid, methacrylic acid, maleic acid, fumaric acid, maleic anhydride, vinyl alcohol, acrylamide, methacrylamide, diacetoneacrylamide, N-vinylpyrrolidone, 2-acrylamido-2-methylpropanesulfonic acid, methacrylsulfonic acid, xylenesulfonic acid and naphthalenesulfonic acid.

A copolymer having styrenesulfonic acid units to be used as the anionic oligomer or polymer providing the counter ion of the above-described quaternary ammonium salt surfactant in the present invention is one having a weight average molecular weight of preferably 300 to 20,000, still more preferably 1,000 to 10,000. Such a copolymer is preferably a (meth)acrylic acid/styrenesulfonic acid copolymer. The molar ratio of the (meth)acrylic acid units to the styrenesulfonic acid units in the copolymer is preferably 0.1 to 10, still more preferably ⅓ to 4.

The acid group (such as a sulfonic acid group and a carboxyl group) in the (co)polymer (2) may be in the form of not only a free acid but also a salt (such as a sodium salt, a potassium salt, an ammonium salt, a diethanolamine salt, a triethanolamine salt, a monoisopropanolamine salt, a diisopropanolamine salt, a triisopropanolamine salt and a 2-amino-2-methylpropane-1,3-diol salt) thereof as long as the effect thereof is not impaired.
(3) Condensates of a sulfonated aromatic compound which may have a hydrocarbon group(s) as a substituent with formaldehyde:

Specific examples of the condensates of a sulfonated aromatic compound with formaldehyde include formaldehyde condensates of petroleum sulfonic acid derivatives, lignin sulfonic acid derivatives, naphthalenesulfonic acid derivatives, xylenesulfonic acid derivatives and alkylbenzenesulfonic acid derivatives.

The above-described condensate (3) according to the present invention is obtained by sulfonating, e.g., naphthalene, an alkyl-substituted benzene, an alkyl-substituted naphthalene, anthracene, an alkyl-substituted anthracene, lignin or an aromatic compound contained in a petroleum residue by an ordinary method and subsequently condensing the resultant sulfonated compound with formaldehyde.

The degree of condensation of the above-described condensate (3) according to the present invention is preferably at least 2, still more preferably 3 to 30. The weight average molecular weight of the condensate (3) is 300 to 20,000.

Various aromatic compounds are usable as the starting material for the above-described condensate (3) and, among them, lignin, xylene, toluene, naphthalene and alkylnaphthalenes of which an alkyl moiety(s) has 1 to 6 carbon atoms are preferred. As a matter of course, a mixture of them is also usable as the starting material. Polycyclic aromatic compounds are preferably used as the starting material for the condensate (3).

A part of the sulfonic acid groups of the above-described condensate (3) may be in the form of its salt such as an alkali metal salt, e.g., a sodium or potassium salt; an alkaline earth metal salt, e.g., a calcium salt; an amine salt and an ammonium salt, as long as the performance reqired in the quaternary ammonium salt surfactant according to the present invention is not impaired.

Among the anionic oligomers and polymers (1) to (3) providing the counter ion of the quaternary ammonium salt surfactant according to the present invention, particularly preferred are condensates, (3), of a sulfonated aromatic compound with formaldehyde. A combination of two or more anionic oligomers (or polymers) may also be used.

The quaternary ammonium salt surfactant in the present invention can be easily produced by bringing a quaternary ammonium salt containing, for example, a halogen atom as the counter ion, into contact with an ion exchange resin to form a quaternary ammonium hydroxide and then reacting the obtained quaternary ammonium hydroxide with the oligomer or polymer (1), (2) or (3) having an anionic residue described above to neutralize it. In this process, it is unnecessary to neutralize all of the anionic residues of the anionic residue-containing oligomer or polymer (1), (2) or (3) with the quaternary ammonium hydroxide. A part of the anionic residues may be in the form of an alkali metal salt, amine salt, organic amine salt or the like, as long as the desired performance of the present invention is not impaired.

At least one surfactant selected from the group consisting of resin acid surfactants and quaternary ammonium salt surfactants represented by the above formula is used as surfactant (B) in the present invention. It is preferred to use one of the resin acid surfactants and quaternary ammonium salt surfactants.

The weight ratio of surfactant (B) to the sorbitan/fatty acid ester surfactant (A) in the present invention is preferably 0.01 to 5, still more preferably 0.02 to 1.

When surfactants (A) and (B) are used in combination with an agricultural chemical, the surfactants are preferably diluted so that the total concentration of them is 100 to 10,000 ppm, particularly 200 to 1,000 ppm.

In the present invention, a surfactant other than surfactants (A) and (B) is also usable in combination with surfactants (A) and (B). Examples of such surfactants include nonionic surfactants, anionic surfactants, cationic surfactants and amphoteric surfactants other than surfactants (A) and (B). They may be used singly, or in the form of a mixture comprising at least two of these surfactants.

Examples of the nonionic surfactants include polyoxyethylene alkyl ethers, polyoxyethylene alkylaryl ethers, polyoxyethylene alkylaryl ether/formaldehyde condensates, polyoxyalkylene aryl ethers, polyoxyalkylene alkyl esters, polyoxyalkylene alkenyl esters, polyoxyalkylene alkylsorbitol esters, polyoxyalkylene alkylglycerol esters, polyoxyalkylene block copolymers, polyoxyalkylene block copolymer/alkylglycerol esters, polyoxyalkylene alkylsulfonamides, polyoxyalkylene oleyl ethers, polyoxyalkylene alkylphenols, alkylglycosides, alkylpolyglycosides, polyoxyalkylene alkylpolyglycosides and polyalkyleneglycerol/fatty acid esters. They may be used singly, or in the form of a mixture comprising at least two of these surfactants.

Among above-described nonionic surfactants, polyethyleneglycerol/fatty acid mono- and diesters are preferred; and polyethyleneglycerol monolaurate and polyethyleneglycerol monooleate are particularly preferred.

Examples of the cationic surfactants include alkylamine/ethylene oxide adducts and alkylamine/propylene oxide adducts, such as an amine derived from tallow, soybean oil fatty acid or coconut oil fatty acid/ethylene oxide adduct, an oleylamine/ethylene oxide adduct, synthetic alkylamine/ethylene oxide adducts and octylamine/ethylene oxide adduct. They may be used singly, or in the form of a mixture comprising at least two of these surfactants.

Among anionic surfactants, typical ones are available in the form of an aqueous solution thereof or a solid. Examples thereof include sodium mono- and dialkylnaphthalenesulfonates, sodium α-olefinsulfonate, sodium alkanesulfonates, alkylsulfosuccinates, alkylsulfates, polyoxyalkylene alkyl ether sulfates, polyoxyalkylene alkyl aryl ether sulfates, polyoxyalkylene styryl phenyl ether sulfates, mono- and dialkylbenzenesulfonates, alkylnaphthalenesulfonates, alkylnaphthalenesulfonate/formaldehyde condensates, alkyl diphenyl ether sulfonates, olefinic sulfonates, mono- and dialkylphosphates, polyoxyalkylene mono- and dialkyl ether phosphates, polyoxyalkylene mono- and diphenyl ether phosphates, polyoxyalkylene mono- and dialkyl phenyl ether phosphates, polycarboxylic acid salts, linear and branched alkyl polyoxyalkylene ether acetic acids and salts thereof, linear and branched alkenyl polyoxyalkylene ether acetic acids and salts thereof, linear and branched alkylamido polyoxyalkylene ether acetic acids and salts thereof, fatty acids such as caprylic acid, lauric acid, stearic acid and oleic acid, and salts thereof, and N-methyl fatty acid taurides. The salt in the above examples refers a sodium salt, a potassium salt, an ammonium salt, an amine salt or the like. They may be used singly, or in the form of a mixture comprising at least two of these surfactants.

Among above-described anionic surfactants, fatty acid salts are preferred; and sodium salts and potassium salts of higher fatty acids such as oleic acid and castor oil fatty acid are particularly preferred.

Examples of the amphoteric surfactants include lauryldimethylamine oxide, Aromox®C/12, Monaterics®, Miranols®, Lonzaines®, and other amine oxides and betaine compounds. They may be used singly, or in the form of a mixture comprising at least two of these surfactants.

The adjuvant composition for agricultural chemicals according to the present invention is employed in the use for enhancing the efficacies of agricultural chemicals.

The adjuvant composition for agricultural chemicals according to the present invention can be used for various crops in safety, without causing injury thereof to the crops.

[Method for enhancing the efficacies of agricultural chemicals]

In the method of the present invention, the above-mentioned adjuvant composition for agricultural chemicals according to the present invention is applied together with an agricultural chemical to a locus which would benefit from such treatment, i.e., the application of the above-mentioned surfactants (A) and (B) together with the agricultural chemical. Specifically, surfactants (A) and (B) and an agricultural chemical are applied to, for example, plants, cereals, vegetables, fruits, trees, fruit trees, grasses, weeds or seeds, and, at the same time, fungi, bacteria, insects, mites or acarids. In other words, the mixture of the adjuvant composition for agricultural chemicals according to the present invention with an agricultural chemical is used in farms, plantations, orchards, gardens, lawns, woods and forests.

Surfactants (A) and (B) are applied to, e.g., plants preferably in the form of a mixture comprising surfactants (A) and (B), an agricultural chemical and an aqueous medium. Specifically, the adjuvant composition for agricultural chemicals of the present invention is added to an agricultural chemical composition which does not contain the adjuvants of the present invention when the agricultural chemical composition is diluted, or, alternatively, an agricultural chemical composition in one of various forms and comprising surfactants (A) and (B) and the agricultural chemical is diluted to thereby prepare a dilution of the agricultural chemical to be used for, for example, spraying, and the dilution is used. The total concentration of surfactants (A) and (B) in the dilution is preferably 100 to 10,000 ppm, still more preferably 200 to 1,000 ppm. Surfactants (A) and (B) are preferably used in such amounts that the weight ratio of the sum of surfactants (A) and (B) to the agricultural chemical is 0.03 to 50. However, when surfactants (A) and (B) are used together with a commercially available agricultural chemical preparation such as Cyhalon, Scout, Nomolt and Milveknock, the weight ratio of the sum of surfactants (A) and (B) to the agricultural chemical may be high, in particular, more than 50 to about 250.

[Agricultural chemical compositions]

The agricultural chemical composition according to the present invention comprises surfactant (A), surfactant (B)

and an agricultural chemical, and the weight ratio of the sum of surfactants (A) and (B) to the agricultural chemical, i.e., [(A)+(B)]/agricultural chemical, is 0.03 to 50, preferably 0.1 to 50, still more preferably 0.3 to 35.

The agricultural chemical composition of the present invention is prepared in any form selected from among, for example, liquid preparations, emulsions, wettable powders, granules, dusts and flowables, the form being not limited. Therefore, the agricultural chemical composition of the present invention may contain other additives such as an emulsifier, a solvent, a dispersant and/or a carrier depending on the formulation or the form thereof.

Such an agricultural chemical composition may further contain a chelating agent, a pH regulator, an inorganic salt or a thickener, if necessary.

Examples of the chelating agents to be used in the agricultural chemical composition of the present invention include those based on aminopolycarboxylic acids, aromatic and aliphatic carboxylic acids, amino acids, ether polycarboxylic acids, phosphonic acids such as iminodimethylphosphonic acids (IDP) and alkyldiphosphonic acids (ADPA), hydroxycarboxylic acids and polyelectrolytes (including oligoelectrolytes); and dimethylglyoxime (DG). These chelating agents may be each in the form of a free acid or a salt such as a sodium salt, a potassium salt and an ammonium salt.

The chelating agent is used in an amount of 0.01 to 30 times by mol the sum of the surfactants in the agricultural chemical composition.

Next, examples of the agricultural chemicals to be used in the agricultural chemical composition of the present invention will be cited, though the agricultural chemicals to be used in the present invention is not restricted thereto.

In the case of fungicides (or bactericides), included are Zineb [zinc ethylenebis(dithiocarbamate)], Maneb [manganese ethylenebis(dithiocarbamate)], Thiram [bis (dimethylthiocarbamoyl) disulfide], Mancozeb [complex of zinc and manganese ethylenebis(dithiocarbamate)], Polycarbamate [dizinc bis(dimethyldithiocarbamate) ethylenebis (dithiocarbamate)], Propineb [polymeric zinc propylenebis (dithiocarbamate)], benzimidazole fungicides such as Benomyl [methyl 1-(butylcarbamoyl)-2-benzimidazolecarbamate] and Thiophanate-methyl [1,2-bis (3-methoxycarbonyl-2-thioureido)benzene]; carboximide fungicides such as Vinclozolin [3-(3,5-dichlorophenyl)-5-methyl-5-vinyl-1,3-oxazolidine-2,4-dione], Iprodione [3-(3, 5-dichlorophenyl)-N-isopropyl-2,4-dioxoimidazolidine-1-carboxamide], Procymidone [N-(3,5-dichlorophenyl)-1,2-dimethylcyclopropane-1,2-dicarboximide]; and, in addition, Anilazine (Triazine) [2,4-dichloro-6-(2-chloroanilino)-1,3, 5-triazine], Triflumizole [(E)-4-chloro-α,α,α-trifluoro-N-(1-imidazol-1-yl-2-propoxyethylidene)-toluidine], Metalaxyl [methyl N-(2-methoxyacetyl)-N-(2,6-xylyl)-DL-alaninate], Bitertanol [all-rac-1-(biphenyl-4-yloxy)-3,3-dimethyl-1-(1H-1,2,4-triazol-1-yl)-2-butan-2-ol], Pyrifenox [2',4'-dichloro-2-(3-pyridyl)acetophenone (EZ)-O-methyloxime], Fenarimol [2,4'-dichloro-α-(pyridin-5-yl) benzhydryl alcohol], Triforine [1,4-bis(2,2,2-trichloro-1-formamidoethyl)piperazine], Iminoctadine acetate [1,1'-iminiodi(octamethylene)diguanidinium triacetate], organocopper compound (Oxine-copper [copper 8-quinolinolate]), cupric hydroxide, antibiotic bactericides (streptomycin type, tetracycline type, polyoxins type, blasticidin S, kasugamycin type, validamycin type), Triadimefon [1-(4-chlorophenoxy)-3,3-dimethyl-1-(1,2,4-triazol-1-yl)-2-butanone], Isoprothiolane [diisopropyl 1,3-dithiolan-2-ylidenemalonate], Chlorothalonil (Daconil, TPN) [tetrachloroisophthalonitrile], Etridiazol (Pansoil) [5-ethoxy-3-trichloromethyl-1,2,4-thiadiazole], Fthalide [4,5,6,7-tetrachlorophthalide], Iprobenfos (Kitazin P) [O,O-diisopropyl-S-benzyl thiophosphate], Edifenphos (Hinosan) [O-ethyl S,S-diphenyl dithiophosphate], Probenazole [3-allyloxy-1,2-benzisothiazole-1,1-dioxide], Captan [N-trichloromethylthiotetrahydrophthalimide] and Fosetyl [aluminum tris(ethylphosphonate)].

In the case of insecticides, included are pyrethroid insecticides such as Permethrin [3-phenoxybenzyl (1RS, 3RS)-(1RS, 3RS)-3-(2,2-dichlorovinyl)-2,2-dimethylcyclopropanecarboxylate], Cypermethrin [(RS)-α-cyano-3-phenoxybenzyl (1RS, 3RS)-(1RS, 3RS)-3-(2,2-dichlorovinyl)-2,2-dimethylcyclopropanecarboxylate], Fenvalerate [α-cyano-3-phenoxybenzyl 2-(4-chlorophenyl) -3-methylbutanoate] and Cyfluthrin (Baythroid) [α-cyano-4-fluoro-3-phenoxyphenylmethyl 3-(2,2-dichloroethenyl)-2, 2-dimethylcyclcopropanecarboxylate]; organophosphorus insecticides such as CYAP (Cyanophos, Cyanox) [pcyanophenyl dimethyl phosphorothioate], DMTP (Methidathion) [S-[(2-methoxy-5-oxo-1,3,4-thiadiazolin-4-yl)methyl]dimethyl phosphorodithioate], BRP (naled) [1,2-dibromo-2,2-dichloroethyl dimethyl phosphate], Salithion (Dioxabenzofes) [2-methoxy 4H-1,3,2-benzodioxaphosphorin 2-sulfide], Dichlorvos (DDVP) [dimethyl 2,2-dichlorovinyl phosphate], Fenitrothion (MEP) [O,O-dimethyl-O-(3-methyl-4-nitrophenyl)thiophosphate], Malathion (Malathon) [S-[1,2-bis(ethoxycarbonyl)ethyl] dimethyl phosphorothiol-thionate], Dimethoate [dimethyl S-(N-methylcarbamoylmethyl)dithiophosphate], Phenthoate (Elsan) [S-[α-(ethoxycarbonyl)benzyl]dimethyl phosphorothiol-thionate] and Fenthion (Baycid) [O,O-dimethyl-O-[3-methyl-4-(methylthio)phenyl] thiophosphate]; carbamate insecticides such as Fenobucarb (Bassa) [O-sec.-butylphenyl methylcarbamate], Metolcarb (MTMC) [m-tolyl methylcarbamate], Xylylcarb (Meobal) [3,4-dimethylphenyl N-methylcarbamate] and Carbaryl (NAC) [1-naphthyl N-methylcarbamate]; Methomyl [S-methyl N-(methylcarbamoyloxy)thioacetimidate] and Cartap [1,3-bis(carbamoylthio)-2-(N,N-dimethylamino)-propane hydrochloride].

Further, in the case of natural insecticides, included are pyrethrin preparations and piperonyl butoxide preparations, which originate from *Chrysanthemum cinerariaefolium*, rotenone preparations, which originate from Derris which is a shrub of the pulse family, and nicotine preparations [containing 3-(1-methyl-2-pyrrolidinyl)pyridine sulfate]. In the case of insect growth regulators (IGR), included are Diflubenzuron [1-(4-chlorophenyl)-3-(2,6-difluorobenzoyl) urea], Teflubenzuron [1-(3,5-dichloro-2,4-difluorophenyl)-3-(2,6-difluorobenzoyl)urea], Chlorofluazuron [1-[3,5-dichloro-4-(3-chloro-5-trifluoromethyl-2-pyridyloxy) phenyl]-3-(2,6-difluorobenzoyl)urea], Buprofezin [2-tert.-butylimino-3-isopropyl-5-phenyl-3,4,5,6-tetrahydro-2H-1, 3,5-thiadiazin-4-one] and Fenoxycarb [ethyl 2-(4-phenoxyphenoxy)ethylcarbamate].

In the case of miticides (or acaricides), included are CPCBS (Chlorfenson) [p-chlorophenyl p-chlorobenzenesulfonate], Phenisobromolate (Bromopropylate) [isopropyl p,p'-dibromobenzilate], Tetradifon [p-chlorophenyl 2,4,5-trichlorophenyl sulfone], Fenothiocarb [S-4-phenoxybutyl dimethyl thiocarbamate], Fenpyroximate [tert.-butyl (E)-α-(1,3-dimethyl-5- phenoxypyrazol-4-ylmethyleneaminooxy)-p-toluate], Fluazinam [3-chloro-N-(3-chloro-5-trifluoromethyl-2-pyridyl)-6-α,α,α-trifluoro-2,6-dinitro-p-toluidine], Clofentezine [3,6-bis(2-chlorophenyl)-1,2,4,5-tetrazine], DPC (Dinocap) [isomeric reaction mixture of 2,6(or 2,4)-dinitro-4-octylphenyl crotonates], Pyridaben [2-tert.-butyl-5-(4-tert.-butylbenzylthio)-4-chloropyridazin-3(2H)-one], Acricid [2,4-dinitro-6-sec.-butylphenyldimethylacrylate], Chloromite [isopropyl 4,4-dichlorobenzylate], Chlorobenzilate (Akar) [ethyl 4,4'-dichlorobenzilate], Dicofol (Kelthane) [1,1-bis(p-chlorophenyl)-2,2,2-trichloroethanol], Benzoximate (Citrazon) [ethyl O-benzoyl-3-chloro-2,6-dimethoxybenzohydroximate], Propargite (Omite) [2-(p-tert.-butylphenoxy)cyclohexyl 2-propynyl sulfite], Fenbutatin Oxide (Osadan) [hexakis(β,β-dimethylphenylethyl)distannoxane], Hexythiazox [trans-5-(4-chlorophenyl)-N-cyclohexyl-4-methyl-2-oxothiazolidine-3-carboxamide] and Amitraz [3-methyl-1,5-bis(2,4-xylyl)-1,3,5-triazapenta-1,4-diene].

In the case of herbicides, included are acid amide herbicides such as Propanil (DCPA) [3',4'-dichloropropionanilide] and Alachlor [2-chloro-2',6'-diethyl-N-(methoxyethyl)acetanilide]; urea herbicides such as Diuron (DCMU) [3-(3,4-dichlorophenyl)-1,1-dimethylurea] and Linuron [3-(3,4-dichlorophenyl)-1-methoxy-1-methylurea); dipyridyl herbicides such as Paraquat Dichloride (Paraquat) [1,1'-dimethyl-4,4'-bipyridirium dichloride] and Diquat Dibromide (Diquat) [6,7-dihydrodipyrido[1,2-a:2',1'-c]pyrazindiium dibromide]; diazine herbicides such as Bromacil [5-bromo-3-sec.-butyl-6-methyluracil]; S-triazine herbicides such as Simazine [2-chloro-4,6-bis(ethylamino)-1,3,5-triazine] and Simetryn [2,4-bis(ethylamino)-6-methylthio-1,3,5-triazine]; nitrile herbicides such as Dichlobeni (DBN) [2,6-dichlorobenzonitrile]; dinitroaniline herbicides such as Trifluralin [α,α,α-trifluoro-2,6-dinitro-N,N-dipropyl-p-toluidine]; carbamate herbicides such as Benthiocarb [S-p-chlorobenzyl diethylthiocarbamate] and MCC [methyl 3,4-dichlorocarbanilate]; diphenylether herbicides such as Nitrofen (NIP) [2,4-dichlorophenyl-p-nitrophenylether]; phenol herbicides such as PCP [pentachlorophenol]; benzoic acid herbicides such as Dicamba (MDBA) [3,6-dichloro-2-methoxybenzoic acid dimethylamine salt]; phenoxy herbicides such as 2,4-D [2,4-dichlorophenoxyacetic acid] and salts (such as sodium and amine) thereof, and Mapica (MCPCA) [2'-chloro-2-(4-chloro-o-tolyloxy)acetanilide]; organophosphorus herbicides such as Glyphosate [N-(phosphonomethyl)glycine] and salts thereof, Bialaphos [sodium salt of L-2-amino-4-[(hydroxy)-(methyl)-phosphinoyl]butyryl-L-alanyl-L-alanine] and Glufosinate [ammonium DL-homoalanin-4-yl (methyl)-phosphinate], and aliphatic herbicides such as TCA sodium salt [sodium trichloroacetate] and Dalapon (DPA) [sodium 2,2-dichloropropionate].

In the case of plant growth regulators, included are MH (maleic hydrazide), Ethephon [2-chloroethylphosphonic acid], UASTA and Bialaphos.

The agricultural chemical composition of the present invention may further contain one or more ingredients such as plant growth regulators other than those cited above, fertilizers and preservatives.

The agricultural chemical composition of the present invention is used in order to control fungi (or bacteria), insects, mites (or acarids) and herbs, or to regulate the growth of plants.

The agricultural chemical composition of the present invention is obtained in, for example, any of the following forms:

(a) all the ingredients are contained in one and the same vessel, (b) the adjuvant composition for agricultural chemicals of the present invention is contained in a vessel, and an agricultural chemical composition which does not contain surfactants (A) and (B) is contained in another vessel, and (c) surfactants (A) and (B) are contained in a vessel, a surfactant other than surfactants (A) and (B) is contained in another vessel, and an agricultural chemical composition which does not contain surfactants (A) and (B) is contained in still another vessel.

The form of each of the contents of the vessels is not particularly limited, and is suitably selected depending on the use and purpose thereof. The material of the vessel is not particularly limited, as long as it does not react with the contents or it does not adversely affect the contents. Examples of the materials include plastics, glasses and foils.

EXAMPLES

The present invention will now be described in more detail by referring to the following Examples which should not be thought to limit the scope of the present invention.

Example 1

Female imagines of Kanzawa spider mite (*Tetranychus kanzawai* Kishida) were applied to kidney bean leaf disks at a ratio of 30 imagines per lot on three runs and then incubated at 25° C. for 24 hours. Then, the whole leaf disks were each dipped in a test solution for 5 seconds. After taking out of the test solution and allowing to stand at 25° C. for 48 hours, the leaf disks were observed and the miticidal ratios were determined on the basis of the result in the untreated lot (refer to the following equation).

$$\text{Miticidal ratio (\%)} = \frac{\text{the number of living mites of an untreated lot} - \text{the number of living mites of a test lot}}{\text{the number of living mites of an untreated lot}} \times 100$$

Nissorun Wettable Powder (containing 10% by weight of Hexythiazox as the active ingredient) and Osadan Wettable Powder 25 (containing 25% by weight of phenbutatin oxide as the active ingredient) as miticides were each diluted 1:3,000 with the use of each of the dilutions (each containing the adjuvant components in a concentration shown in Table 1 or 2) obtained by diluting the adjuvant compositions for agricultural chemicals shown in Tables 1 and 2 with city water at a ratio of 1:1,000, and the dilutions thus obtained were each used. Further, the above procedure was repeated without using any adjuvant composition.

The results are given in Tables 1 and 2.

TABLE 1

| Composition (% by wt.) | (A)/(B) by wt. | Acitive ingredient concn.* (ppm) | Miticidal raio (%) Kanzawa spider mite | |
|---|---|---|---|---|
| | | | Osadan Wettable Powder 25 | Nissorun Wettable Powder |
| Without adjuvant composn. (agr. chem. only) | | | 45.6 | 47.8 |
| Sorbitan monolaurate/IFA | | | | |
| = 30/70 | — | 300 | 52.2 | 54.4 |
| = 40/60 | — | 400 | 54.5 | 58.9 |
| = 50/50 | — | 500 | 61.6 | 62.2 |
| = 60/40 | — | 600 | 68.9 | 71.1 |
| = 70/30 | — | 700 | 74.4 | 73.3 |
| = 80/20 | — | 800 | 78.9 | 77.8 |
| Sorbitan monopalmitate/IPA | | | | |
| = 5/50 | — | 500 | 65.6 | 66.7 |
| = 60/40 | — | 600 | 71.1 | 74.4 |
| = 70/30 | — | 700 | 73.3 | 76.7 |
| Sorbitan monostearate/IPA = 60/40 | — | 600 | 73.3 | 77.9 |
| Sorbitan monooleate/IPA = 60/40 | — | 600 | 62.2 | 56.7 |
| Sorbitan monolaurate/POE (18) resin acid/anion/IPA | | | | |
| = 70/3/4/23 | 1/0.043 | 730 | 91.1 | 92.2 |
| = 70/6/4/20 | 1/0.086 | 760 | 87.8 | 96.7 |
| = 70/10/4/16 | 1/0.143 | 800 | 97.8 | 97.8 |
| = 70/20/4/6 | 1/0.286 | 900 | 100.0 | 98.9 |
| = 75/6/4/15 | 1/0.080 | 810 | 100.0 | 97.8 |
| = 80/6/4/10 | 1/0.075 | 860 | 100.0 | 100.0 |
| = 60/6/4/30 | 1/0.100 | 660 | 90.0 | 88.9 |
| Sorbitan monolaurate/POE (9) resin acid/anion/IPA = 75/6/4/15 | 1/0.086 | 810 | 93.3 | 95.6 |
| Sorbitan monolaurate/POE (15) resin acid/anion/IPA = 75/6/4/15 | 1/0.086 | 810 | 97.8 | 97.8 |
| Sorbitan monolaurate/POE (20) resin acid/anion/IPA = 75/6/4/15 | 1/0.086 | 810 | 94.4 | 100.0 |
| Sorbitan monolaurate/POE (30) resin acid/anton/IPA = 75/6/4/15 | 1/0.086 | 810 | 94.4 | 91.1 |
| Sorbitan monolaurate/POE (18) resin acid/anion/IPA | | | | |
| = 30/20/4/46 | 1/0.667 | 500 | 92.2 | 90.0 |
| = 30/30/4/36 | 1/1.000 | 600 | 93.3 | 96.7 |
| = 25/25/4/46 | 1/1.000 | 500 | 90.0 | 90.0 |
| =35/3/4/58 | 1/0.086 | 380 | 91.1 | 85.9 |
| Sorbitan monolaurate/quat. ammonium salt-1/nonion/IPA | | | | |
| = 30/5/30/35 | 1/0.167 | 350 | 75.6 | 78.9 |
| = 40/5/30/25 | 1/0.125 | 450 | 88.9 | 84.4 |
| = 50/5/30/15 | 1/0.100 | 550 | 91.1 | 88.9 |
| = 60/5/30/5 | 1/0.083 | 650 | 94.4 | 96.7 |
| = 70/5/20/5 | 1/0.080 | 750 | 97.8 | 95.9 |
| = 50/10/30/10 | 1/0.714 | 600 | 98.8 | 94.4 |
| = 50/15/30/5 | 1/0.300 | 650 | 96.7 | 97.8 |

TABLE 2

| Composition (% by wt.) | (A)/(B) by wt. | Acitive ingredient concn.* (ppm) | Miticidal raio (%) Kanzawa spider mite | |
|---|---|---|---|---|
| | | | Osadan Wettable Powder 25 | Nissorun Wettable Powder |
| Without adjuvant composn. (agr. chem. only) | | | 45.6 | 47.8 |
| Sorbitan monolaurate/anion/IPA = 70/4/26 | — | 700 | 75.6 | 73.3 |

TABLE 2-continued

| Composition (% by wt.) | (A)/(B) by wt. | Acitve ingredient concn.* (ppm) | Miticidal raio (%) Kanzawa spider mite | |
|---|---|---|---|---|
| | | | Osadan Wettable Powder 25 | Nissorun Wettable Powder |
| POE (18) resin acid/anion/IPA | | | | |
| = 6/4/90 | — | 60 | 51.1 | 48.9 |
| = 10/4/86 | — | 100 | 53.3 | 52.2 |
| = 20/4/76 | — | 200 | 54.4 | 33.6 |
| Quat. ammonium salt-1/ nonion/IPA = 5/30/65 | — | 50 | 53.3 | 51.1. |
| Nonion/IPA = 30/70 | — | — | 48.9 | 47.8 |
| POE (20) sorbitan monolaurate/IPA | | | | |
| = 50/50 | — | 500 | 60.0 | 58.9 |
| = 60/40 | — | 600 | 65.6 | 64.4 |
| = 70/30 | — | 700 | 71.1 | 67.8 |
| POE (20) sorbitan monolaurate/IPA = 60/40 | — | 600 | 60.0 | 61.i |
| POE (20) sorbitan monopalmitate/ IPA = 60/40 | — | 600 | 58.9 | 55.6 |
| POE (20) sorbitan monostearate/ IPA = 60/40 | — | 600 | 58.9 | 54.4 |
| POE (20) sorbitan monooleate/IPA = 60/40 | — | 600 | 53.3 | 48.9 |
| Sorbitan monolaurate/POE (5) sorbitan monolaulate/POE (18) resin acid/IPA = 50/10/10/30 | 1/0.200/ 0.200 (1/0.167) | 700 | 87.8 | 86.7 |
| POE (5) sorbitan monolaurate/ POE (18) resin acid/IPA | | | | |
| = 70/6/24 | 1/0.086 | 760 | 81.1 | 82.2 |
| = 75/6/19 | 1/0.086 | 810 | 85.6 | 90.0 |
| POE (5) sorbitan monolaurate/ quat. ammonium salt-1/nonion/IPI = 50/10/30/10 | 1/0.200 | 600 | 75.6 | 71.1 |
| Sorbitan monolaurate/POE (5) sorbitan monolaurate/quat. ammonium salt-1/nonion = 50/10/10/30 | 1/0.200/ 0.200 (1/0.167) | 700 | 94.4 | 93.3 |

In Tables, "POE (n) resin acid" refers to a compound wherein n mol, on the average, of ethylene oxide is added to 1 mol of resin acid. This compound contains a functional group represented by the formula: —CO(OE)$_n$OH, wherein OE represents an oxyethylene, and may also be called "POE (n) rosin", "POE (n) rosin acid", "POE (n) rosin ether", "POE (n) resin acid ether" or "POE (n) rosin acid ester".

Further, in Tables, "IPA" refers to isopropyl alcohol, "anion" to a castor oil fatty acid soap (potassium salt), "nonion" to a polyoxyethylene (average number of moles of ethylene oxide added: 8) monooleate, and "quat. ammonium salt-1" to a compound having the following chemical structure:

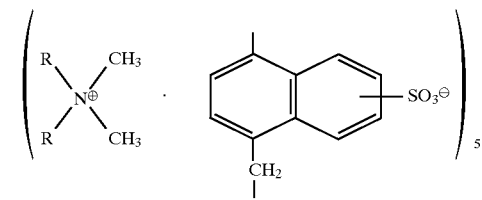

[R = C$_{12}$H$_{25}$]

The same will apply in the following Examples.

Example 2

The same test as that of Example 1 was repeated except that the female imagines of Kanzawa spider mite were replaced by imagines of green peach aphid (*Myzus persicae* Sulzer) and that Elsan Emulsion (containing 50% by weight of ethyl dimethyldithiophosphorylphenylacetate as the active ingredient) was used as the insecticide.

The results are given in Tables 3 and 4.

TABLE 3

| Composition (% by wt.) | (A)/(B) by wt. | Active ingredient concn.* (ppm) | Insecticidal ratio (%) Green peach aphid Elsan Emulsion |
|---|---|---|---|
| Without adjuvant composn. (agr. chem. only) | | | 55.6 |
| Sorbitan monolaurate/IPA | | | |
| = 30/70 | — | 300 | 61.1 |
| = 40/60 | — | 400 | 68.9 |
| = 50/50 | — | 500 | 70.0 |
| = 60/40 | — | 600 | 74.4 |
| = 70/30 | — | 700 | 77.8 |
| = 80/20 | — | 800 | 80.0 |
| Sorbitan monopalmitate/IPA | | | |
| = 50/50 | — | 500 | 72.2 |
| = 60/40 | — | 600 | 75.6 |
| = 70/30 | — | 700 | 80.0 |
| Sorbitan monostearate/IPA = 60/40 | — | 600 | 77.8 |
| Sorbitan monooleate/IPA = 60/40 | — | 600 | 68.9 |
| Sorbitan monolaurate/POE (18) resin acid/anion/IPA | | | |
| = 70/3/4/23 | 1/0.043 | 730 | 94.4 |
| = 70/6/4/20 | 1/0.086 | 760 | 95.6 |
| = 70/10/4/16 | 1/0.143 | 800 | 100.0 |
| = 70/20/4/6 | 1/0.286 | 900 | 100.0 |
| = 75/6/4/15 | 1/0.080 | 810 | 96.8 |
| = 80/6/4/10 | 1/0.075 | 860 | 100.0 |
| = 60/6/4/30 | 1/0.100 | 660 | 93.3 |
| Sorbitan monolaurate/POE (9) resin acid/anion/IPA = 75/6/4/15 | 1/0.086 | 810 | 92.2 |
| Sorbitan monolaurate/POE (15) resin acid/anion/IPA = 75/6/4/15 | 1/0.086 | 810 | 95.6 |
| Sorbitan monolaurate/POE (20) resin acid/anion/IPA = 75/6/4/15 | 1/0.086 | 810 | 98.9 |
| Sorbitan monolaurate/POE (30) resin acid/anion/IPA = 75/6/4/15 | 1/0.086 | 810 | 98.9 |
| Sorbitan monolaurate/POE (18) resin acid/anion/IPA | | | |
| = 30/20/4/46 | 1/0.667 | 500 | 88.6 |
| = 30/30/4/36 | 1/1.000 | 600 | 88.9 |
| = 25/25/4/46 | 1/1.000 | 500 | 88.9 |
| = 35/3/4/58 | 1/0.086 | 380 | 88.9 |
| Sorbitan monolautate/quat. ammonium salt-1/nonion/IPA | | | |
| = 30/5/30/35 | 1/0.167 | 350 | 74.4 |
| = 40/5/30/25 | 1/0.125 | 450 | 76.7 |
| = 50/5/30/15 | 1/0.100 | 550 | 85.6 |
| = 60/5/30/5 | 1/0.083 | 650 | 93.3 |
| = 70/5/20/5 | 1/0.080 | 750 | 96.7 |
| = 50/10/30/10 | 1/0.714 | 600 | 91.1 |
| = 50/15/30/5 | 1/0.300 | 650 | 98.9 |

TABLE 4

| Composition (% by wt.) | (A)/(B) by wt. | Active ingredient concn.* (ppm) | Insecticidal ratio (%) Green peach aphid Elsan Emulsion |
|---|---|---|---|
| Without adjuvant composn. (agr. chem. only) | | | 55.6 |
| Sorbitan monolaurate/anion/IPA = 70/4/26 | — | 700 | 80.0 |
| POE (18) resin acid/anion/IPA | | | |
| = 6/4/90 | — | 60 | 56.7 |
| = 10/4/86 | — | 100 | 60.0 |
| = 20/4/76 | — | 200 | 63.3 |
| Quat. ammonium salt 1/ | — | 50 | 60.0 |

TABLE 4-continued

| Composition (% by wt.) | (A)/(B) by wt. | Active ingredient concn.* (ppm) | Insecticidal ratio (%) Green peach aphid Elsan Emulsion |
|---|---|---|---|
| nonion/IPA = 5/30/65 | | | |
| Nonion/IPA = 30/70 | — | — | 56.7 |
| POE (20) sorbitan monolaurate/IPA | | | |
| = 50/50 | — | 500 | 64.4 |
| = 60/40 | — | 600 | 72.2 |
| = 70/30 | — | 700 | 72.2 |
| POE (20) sorbitan monolaurate/IPA = 60/40 | — | 600 | 68.9 |
| POE (20) sorbitan monopalmitate/IPA = 60/40 | — | 600 | 66.7 |
| POE (20) sorbitan monostearate/IPA = 60/40 | — | 600 | 67.8 |
| POE (20) sorbitan monooleate/IPA = 60/40 | — | 600 | 60.0 |
| Sorbitan monolaurate/POE (5) sorbitan monolaurate/POE (18) resin acid/IPA = 50/10/10/30 | 1/0.200/ 0.200 (1/0.167) | 700 | 86.6 |
| POE (5) sorbitan monolaurate/ POE (18) resin acid/IPA | | | |
| = 70/6/24 | 1/0.086 | 760 | 78.9 |
| = 75/6/19 | 1/0.056 | 810 | 86.7 |
| POE (5) sorbitan monolaurate/ quat. ammonium salt-1/nonion/IPA = 50/10/30/10 | 1/0.200 | 600 | 72.2 |
| Sorbitan monolaurate/POE (5) sorbitan monolaurate/quat. ammonium sait-1/nonion = 50/10/10/30 | 1/0.200/ 0.200 (1/0.167) | 700 | 91.1 |

Example 3

A spore suspension ($10^7$/ml) of cucumber *Botrytis cinerea* acquiring the resistance against fungicides was applied to young cucumber seedlings at the trifoliate stage in a dose of 10 ml per pot and the resulting seedlings were allowed to stand at 25° C. under a relative humidity of 90% for one day.

Then, a commercially available fungicide, i.e., Rovral Wettable Powder [containing 50% by weight of 3-(3,5-dichlorophenyl)-N-isopropyl-2,4-dioxoimidazoline-1-carboxamide as the active ingredient] was diluted 1:2,000 with the use of each of the dilutions (each containing the adjuvant components in a concentration shown in Table 5 or 6) obtained by diluting the adjuvant compositions for agricultural chemicals shown in Tables 5 and 6 with city water at a ratio of 1:1,000. The dilutions thus prepared were each applied to the seedlings in a dose of 5 ml per pot. After allowing the pots to stand at 25° C. under a relative humidity of 85%, lesions were counted and the preventive value was calculated in accordance with the following equation. Further, the above procedure was repeated without using any adjuvant composition.

The results are given in Tables 5 and 6.

$$\text{preventive value} = \left[ 1 - \frac{\text{no. of lesions of a test lot}}{\text{no. of lesion of an untreated lot}} \right] \times 100$$

TABLE 5

| Composition (% by wt.) | (A)/(B) by wt. | Active ingredient concn.* (ppm) | Preventive value *Botrytis cinerea* Rovral Wettable Powder |
|---|---|---|---|
| Without adjuvant composn. (agr. chem. only) | | | 41.1 |
| Sorbitan monolaurate/IPA | | | |
| = 30/70 | — | 300 | 48.2 |
| = 40/60 | — | 400 | 50.2 |
| = 50/50 | — | 500 | 60.5 |
| = 60/40 | — | 600 | 63.2 |
| = 70/30 | — | 700 | 67.4 |
| = 80/20 | — | 800 | 70.3 |
| Sorbitan monopalmitate/IPA | | | |
| = 50/50 | — | 500 | 59.4 |
| = 60/40 | — | 600 | 64.2 |
| = 70/30 | — | 700 | 66.6 |

TABLE 5-continued

| Composition (% by wt.) | (A)/(B) by wt. | Active ingredient concn.* (ppm) | Preventive value Botrytis cinerea Rovral Wettable Powder |
|---|---|---|---|
| Sorbitan monostearate/IPA = 60/40 | — | 600 | 60.4 |
| Sorbitan monooleate/IPA = 60/40 | — | 600 | 65.6 |
| Sorbitan monolaurate/POE (18) resin acid/anion/IPA | | | |
| = 70/3/4/23 | 1/0.043 | 730 | 85.4 |
| = 70/6/4/20 | 1/0.086 | 760 | 90.6 |
| = 70/10/4/16 | 1/0.143 | 800 | 93.3 |
| = 70/20/4/6 | 1/0.286 | 900 | 95.1 |
| = 75/6/4/15 | 1/0.080 | 810 | 95.2 |
| = 80/6/4/10 | 1/0.075 | 860 | 97.9 |
| = 60/6/4/30 | 1/0.100 | 660 | 90.2 |
| Sorbitan monolaurate/POE (9) resin acid/anion/IPA = 75/6/4/15 | 1/0.086 | 810 | 94.8 |
| Sorbitan monolaurate/POE (15) resin acid/anion/IPA = 75/6/4/15 | 1/0.086 | 810 | 95.6 |
| Sorbitan monolaurate/POE (20) resin acid/anion/IPA = 75/6/4/15 | 1/0.086 | 810 | 98.8 |
| Sorbitan monolaurate/POE (30) resin acid/anion/IPA = 75/6/4/15 | 1/0.086 | 810 | 97.7 |
| Sorbitan monolaurate/POE (18) resin acid/anion/IPA | | | |
| = 30/20/4/46 | 1/0.667 | 500 | 57.9 |
| = 30/30/4/36 | 1/1.000 | 600 | 66.9 |
| = 25/25/4/46 | 1/1.000 | 500 | 60.6 |
| = 35/3/4/58 | 1/0.086 | 380 | 65.2 |
| Sorbitan monolaurate/quat. ammonium salt-1/nonion/IPA | | | |
| = 30/5/30/35 | 1/0.167 | 350 | 72.5 |
| = 40/5/30/25 | 1/0.125 | 450 | 76.6 |
| = 50/5/30/15 | 1/0.100 | 550 | 80.0 |
| = 60/5/30/5 | 1/0.083 | 650 | 84.4 |
| = 70/5/20/5 | 1/0.080 | 750 | 88.4 |
| = 50/10/30/10 | 1/0.714 | 600 | 91.4 |
| = 50/15/30/5 | 1/0.300 | 650 | 94.4 |

TABLE 6

| Composition (% by wt.) | (A)/(B) by wt. | Active ingredient concn.* (ppm) | Preventive value Botrytis cinerea Rovral Wettable Powder |
|---|---|---|---|
| Without adjuvant composn. (agr. chem. only) | | | 41.1 |
| Sorbitan monolaurate/anion/IPA = 70/4/26 | — | 700 | 65.3 |
| POE (18) resin acid/anion/IPA | | | |
| = 6/4/90 | — | 60 | 43.2 |
| = 10/4/86 | — | 100 | 45.2 |
| = 20/4/76 | — | 200 | 45.5 |
| Quat. ammonium salt-1/nonion/IPA = 5/30/65 | — | 50 | 65.0 |
| Nonion/IPA = 30/70 | — | — | 44.9 |
| POE (20) sorbitan monolaurate/IPA | | | |
| = 50/50 | — | 500 | 58.8 |
| = 60/40 | — | 600 | 59.8 |
| = 70/30 | — | 700 | 61.2 |
| POE (20) sorbitan monolaurate/IPA = 60/40 | — | 600 | 33.3 |
| POE (20) sorbitan monopalmitate/IPA = 60/40 | — | 600 | 50.2 |
| POE (20) sorbitan monostearate/IPA = 60/40 | — | 600 | 50.9 |
| POE (20) sorbitan monooleate/IPA = | — | 600 | 67.2 |

TABLE 6-continued

| Composition (% by wt.) | (A)/(B) by wt. | Active ingredient concn.* (ppm) | Preventive value Botrytis cinerea Rovral Wettable Powder |
|---|---|---|---|
| 60/40 | | | |
| Sorbitan monolaurate/POE (5) sorbitan monolaurate/POE (18) resin acid/IPA = 50/10/10/30 POE (5) sorbitan monolaurate/ POE (18) resin acid/IPA | 1/0.200/ 0.200 (1/0.167) | 700 | 72.2 |
| = 70/6/24 | 1/0.086 | 760 | 70.0 |
| = 75/6/19 | 1/0.086 | 810 | 80.9 |
| POE (5) sorbitan monolaurate/ quat. ammonium salt-1/nonion/IPA = 50/10/30/10 | 1/0.200 | 600 | 79.9 |
| Sorbitan monolaurate/POE (5) sorbitan monolaurate/quat. ammonium salt-1/nonion = 50/10/10/30 | 1/0.200/ 0.200 (1/0.167) | 700 | 94.6 |

We claim:

1. An adjuvant composition for agricultural chemicals comprising at least one sorbitan/fatty acid ester surfactant (A) and at least one surfactant (B) selected from the group consisting of resin acid surfactants and quaternary ammonium salt surfactants represented by the following formula:

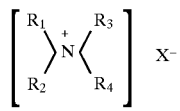

wherein at least one of $R_1$, $R_2$ and $R_3$ represents a linear or branched alkyl or alkenyl group having 8 to 30 carbon atoms, and the rest of them represent(s) one or two groups selected from the group consisting of —$CH_3$, —$CH_2CH_3$,

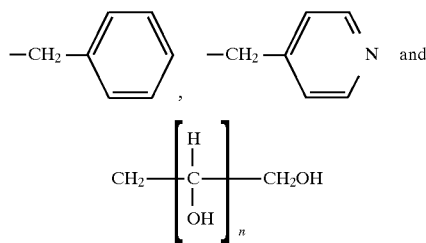

(n being a number of 1 to 5), $R_4$ represents —$CH_3$ or —$CH_2CH_3$, and the counter ion, $X^-$, represents an anionic group derived from an anionic oligomer or polymer having a weight average molecular weight of 300 to 20,000 and selected from the group consisting of (1) (co)polymers obtained by polymerizing a monomer (s) which comprises at least one member selected from the group consisting of unsaturated carboxylic acids and derivatives thereof as the indispensable component, (2) (co)polymers obtained by polymerizing a monomer(s) which comprises styrenesulfonic acid as the indispensable component, and (3) condensates of a sulfonated aromatic compound which may have a hydrocarbon group(s) as a substituent with formaldehyde; wherein the weight ratio of surfactant (B) to surfactant (A) is between 0.02 and 1.

2. The adjuvant composition for agricultural chemicals according to claim 1, which further comprises at least one surfactant(s) other than surfactants (A) and (B).

3. The adjuvant composition for agricultural chemicals according to claim 1, wherein the sorbitan/fatty acid ester surfactant (A) is at least one member(s) selected from the group consisting of sorbitan/fatty acid esters and polyoxyalkylene sorbitan/fatty acid esters.

4. The adjuvant composition for agricultural chemicals according to claim 1, wherein the sorbitan/fatty acid ester surfactant (A) is a sorbitan/fatty acid ester.

5. The adjuvant composition for agricultural chemicals according to claim 1, wherein the resin acid surfactant (B) is a polyoxyalkylene tall rosin.

6. The adjuvant composition for agricultural chemicals according to claim 5, wherein the polyoxyalkylene tall rosin is one obtained by adding, on average, 5 to 40 mol, per mol of a tall rosin, of an alkylene oxide to the tall rosin.

7. The adjuvant composition for agricultural chemicals according to claim 5, wherein the polyoxyalkylene tall rosin is one obtained by adding, on average, 5 to 40 mol, per mol of a tall rosin, of an alkylene oxide(s) as the indispensable component to the tall rosin.

8. The adjuvant composition of claim 7, wherein the alkylene oxide is ethylene oxide.

9. The adjuvant composition for agricultural chemicals according to claim 1, wherein the resin acid surfactant (B) is a polyoxyalkylene resin acid.

10. The adjuvant composition for agricultural chemicals according to claim 9, wherein the polyoxyalkylene resin acid is one obtained by adding, on average, 5 to 40 mol, per mol of a resin acid, of an alkylene oxide to the resin acid.

11. The adjuvant composition for agricultural chemicals according to claim 9, wherein the polyoxyalkylene resin acid is one obtained by adding, on average, 5 to 40 mol, per mol of a resin acid, of an alkylene oxide(s) as the indispensable component to the resin acid.

12. The adjuvant composition of claim 11, wherein the alkylene oxide is ethylene oxide.

13. The adjuvant composition of claim 1, wherein the weight ratio of surfactant (B) to surfactant (A) is approximately 0.043.

14. The adjuvant composition of claim 1, wherein the weight ratio of surfactant (B) to surfactant (A) is approximately 0.086.

15. The adjuvant composition of claim 1, wherein the weight ratio of surfactant (B) to surfactant (A) is approximately 0.143.

16. The adjuvant composition of claim 1, wherein the weight ratio of surfactant (B) to surfactant (A) is approximately 0.286.

17. The adjuvant composition of claim 1, wherein the weight ratio of surfactant (B) to surfactant (A) is approximately 0.080.

18. The adjuvant composition of claim 1, wherein the weight ratio of surfactant (B) to surfactant (A) is approximately 0.075.

19. The adjuvant composition of claim 1, wherein the weight ratio of surfactant (B) to surfactant (A) is approximately 0.100.

20. A method for enhancing the efficacy of an agricultural chemical, which comprises applying a sorbitan/fatty acid ester surfactant (A) and at least one surfactant (B) selected from the group consisting of resin acid surfactants and quaternary ammonium salt surfactants represented by the following formula together with an agricultural chemical to a locus which would benefit from such treatment:

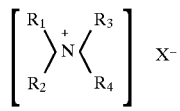

wherein at least one of $R_1$, $R_2$ and $R_3$ represents a linear or branched alkyl or alkenyl group having 8 to 30 carbon atoms, and the rest of them represent(s) one or two groups selected from the group consisting of —$CH_3$, —$CH_2CH_3$,

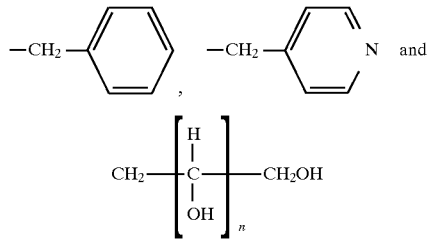

(n being a number of 1 to 5), $R_4$ represents —$CH_3$ or —$CH_2CH_3$, and the counter ion, $X^-$, represents an anionic group derived from an anionic oligomer or polymer having a weight average molecular weight of 300 to 20,000 and selected from the group consisting of (1) (co)polymers obtained by polymerizing a monomer (s) which comprises at least one member selected from the group consisting of unsaturated carboxylic acids and derivatives thereof as the indispensable component, (2) (co)polymers obtained by polymerizing a monomer(s) which comprises styrenesulfonic acid as the indispensable component, and (3) condensates of a sulfonated aromatic compound which may have a hydrocarbon group(s) as a substituent with formaldehyde; wherein the weight ratio of surfactant (B) to surfactant (A) is between 0.02 and 1.

21. The method for enhancing the efficacy of an agricultural chemical according to claim 20, wherein a surfactant other than surfactants (A) and (B) is also used together with an agricultural chemical.

22. The method for enhancing the efficacy of an agricultural chemical according to claim 20, wherein the weight ratio of the sum of surfactants (A) and (B) to the agricultural chemical is 0.03 to 50.

23. The method for enhancing the efficacy of an agricultural chemical according to claim 20, wherein the agricultural chemical is a fungicide, an insecticide, a miticide, a herbicide or a plant growth regulator.

24. An agricultural chemical composition comprising at least one sorbitan/fatty acid ester surfactant (A), and at least one surfactant (B) selected from the group consisting of resin acid surfactants and quaternary ammonium salt surfactants represented by the following formula, and an agricultural chemical, wherein the weight ratio of the sum of surfactants (A) and (B) to the agricultural chemical is 0.03 to 50:

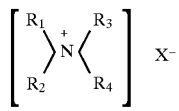

wherein at least one of $R_1$, $R_2$ and $R_3$ represents a linear or branched alkyl or alkenyl group having 8 to 30 carbon atoms, and the rest of them represent(s) one or two groups selected from the group consisting of —$CH_3$, —$CH_2CH_3$,

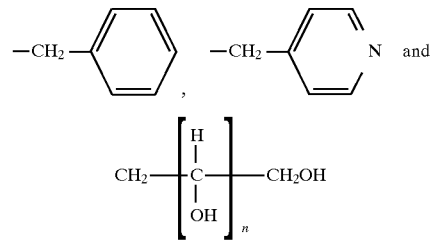

(n being a number of 1 to 5), $R_4$ represents —$CH_3$ or —$CH_2CH_3$, and the counter ion, $X^-$, represents an anionic group derived from an anionic oligomer or polymer having a weight average molecular weight of 300 to 20,000 and selected from the group consisting of (1) (co)polymers obtained by polymerizing a monomer (s) which comprises at least one member selected from the group consisting of unsaturated carboxylic acids and derivatives thereof as the indispensable component, (2) (co)polymers obtained by polymerizing a monomer(s) which comprises styrenesulfonic acid as the indispensable component, and (3) condensates of a sulfonated aromatic compound which may have a hydrocarbon group(s) as a substituent with formaldehyde; wherein the weight ratio of surfactant (B) to surfactant (A) is between 0.02 and 1.

25. The agricultural chemical composition according to claim 24, which further comprises at least one surfactant(s) other than surfactants (A) and (B).

26. The agricultural chemical composition according to claim 24, wherein the agricultural chemical is a fungicide, an insecticide, a miticide, a herbicide or a plant growth regulator.

* * * * *